United States Patent [19]  
Evans et al.

[11] Patent Number: 5,091,387  
[45] Date of Patent: Feb. 25, 1992

[54] SPIROCYCLIC OXYTOCIN ANTAGONISTS

[75] Inventors: Ben E. Evans, Lansdale; Douglas J. Pettibone, Chalfont; Roger M. Friedinger, Lansdale, all of Pa.

[73] Assignee: Merck & Co., Inc., Rahway, N.J.

[21] Appl. No.: 742,713

[22] Filed: Aug. 5, 1991

Related U.S. Application Data

[63] Continuation of Ser. No. 488,343, Mar. 2, 1990, abandoned.

[51] Int. Cl.$^5$ .................. A61K 31/445; A61K 31/40; C07D 295/00
[52] U.S. Cl. .................................. 514/278; 514/409; 546/17; 548/411
[58] Field of Search ............ 546/17; 548/411; 514/278, 409

[56] References Cited

U.S. PATENT DOCUMENTS 3,654,287 4/1972 Dekstra ........................ 546/17
3,666,764 5/1972 Campbell et al. ............. 546/17
4,379,933 4/1983 Ong et al. ..................... 546/17

OTHER PUBLICATIONS

Campbell, *J. Chem. Soc.* (1954) pp. 1377-1380.
Crooks et al., *J. Med. Chem.* (1980), vol. 23, pp. 679-682.
Crooks et al., *J. Pharm. Sci.*, (1982), vol. 71, 3, pp. 291-294.
Janssen, Chem. Abst. 60-645e (1964).
Sawyer et al., "ISI Atlas of Science: Pharmacology" (1988) pp. 252-256.
Matier et al., J. Orig. Chem. (1971) vol. 36, 5, pp. 650-654.
Greifenstein et al., J. Orig. Chem., (1981) vol. 46, pp. 5125-5132.
Laus et al., *Heterocycles* (1984), vol. 22, 2, pp. 311-331.
Ansell, Ed., "Rodd's Chem. of Carbon Compounds" (1984) Elsevier Scientific Publishing Co., New York, pp. 166-174.
Bosch et al., *Can. J. Chem.* (1964) vol. 42, pp. 1718-1735.
Coffey, Ed., "Rodd's Chemistry of Carbon Compounds" (1978) Elsevier Scientific Publishing Co., New York, pp. 82-97.
Jayamani et al., *Synthetic Communications* (1985), vol. 15, 6 pp. 535-542.
Anstead et al., *J. Med. Chem.* (1988), vol. 31, pp. 1316-1326.
Ganellin et al., *Chemistry and Industry* (1965), pp. 1256-1257.
Dykstra et al., *J. Med. Chem.* (1967) vol. 19, pp. 418-428.

*Primary Examiner*—Cecilia Shen
*Attorney, Agent, or Firm*—Frank P. Grassler; Richard S. Parr; Charles M. Caruso

[57] ABSTRACT

Disclosed are spirocyclic compounds of the formula:

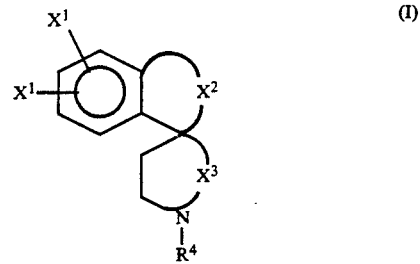

The compounds of formula I are oxytocin antagonists useful in the treatment of preterm labor and dysmenorrhea, and for the stoppage of labor preporatory to Caesarian delivery. Also disclosed are pharmaceutical compositions containing these compounds as well as methods for preparing the compounds.

4 Claims, No Drawings

SPIROCYCLIC OXYTOCIN ANTAGONISTS

This application is a file wrapper continuation of application Ser. No. 07/488,343, filed on Mar. 2, 1990 now abandoned.

BACKGROUND OF THE INVENTION

This invention pertains to the field of obstetrics. In the field of obstetrics, one of the most important problems is the management of preterm labor. A significant number of the pregnancies progressing past 20 weeks of gestation experience premature labor and delivery which is a leading cause of neonatal morbidity and mortality.

It has recently been proposed that a selective oxytocin antagonist would be the ideal tocolytic agent. In the last few years, evidence has accumulated to suggest strongly that oxytocin is the physiological initiator of labor in several mammalian species including humans. Oxytocin is believed to exert this effect in part by directly contracting the uterine myometrium and in part by enhancing the synthesis and release of contractile prostaglandins from the uterine endometrium/decidua. These prostaglandins may, in addition, be important in the cervical ripening process. By these mechanisms, the process of labor (term and preterm) is initiated by a heightened sensitivity of the uterus to oxytocin, resulting in part by a well-documented increase in the number of oxytocin receptors in this tissue. This 'up-regulation' of oxytocin receptors and enhanced uterine sensitivity appears to be due to trophic effects of rising plasma levels of estrogen towards term. By blocking both the direct (contractile) and indirect (enhanced prostaglandin synthesis) effects of oxytocin on the uterus, a selective oxytocin antagonist would likely be more efficacious for treating preterm labor than current regimens. In addition, since oxytocin at term has major effects only on the uterus, such a compound would be expected to have few, if any, side effects.

The compounds of the present invention may also be useful for the treatment of dysmenorrhea. This condition is characterized by cyclic pain associated with menses during ovulatory cycles. The pain is thought to result from uterine contractions and ischemia, probably mediated by the effect of prostaglandins produced in the secretory endometrium. By blocking both the direct and indirect effects of oxytocin on the uterus, a selective oxytocin antagonist may be more efficacious for treating dysmenorrhea than current regimens.

An additional use for the present invention is for the stoppage of the labor preparatory to Caesarian delivery. Certain spiroindanylpiperidines and spiroindenylpiperidines are known (U.S. Pat. Nos. 3,654,287 and 3,666,764), however, they are reported to be useful as anesthetic agents which is quite distinct from the utility of the present invention.

It was, therefore, a purpose of this invention to identify substances which more effectively antagonize the function of oxytocin in disease states in animals, preferably mammals, especially in humans. It was another purpose of this invention to prepare novel compounds which more selectively inhibit oxytocin. It was still another purpose of this invention to develop a method of antagonizing the functions of oxytocin in disease states in mammals. It is also a purpose of this invention to develop a method of preventing or treating oxytocin related disorders of particularly preterm labor and dysmenorrhea.

SUMMARY OF THE INVENTION

It has now been found that compounds of Formula I are antagonists of oxytocin and bind to the oxytocin receptor. These compounds are useful in the treatment and prevention of oxytocin-related disorders of animals, preferably mammals and especially humans. These disorders are primarily preterm labor and dysmenorrhea. The compounds would also find usefulness for stoppage of labor preparatory to Caesarian delivery.

DETAILED DESCRIPTION OF THE INVENTION

The present invention concerns compounds of the formula:

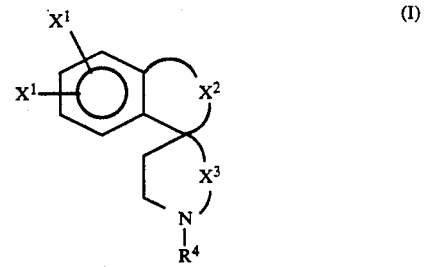

wherein:

$X^1$ is hydrogen, $C_{1-6}$ linear or branched chain alkyl, lower alkenyl, lower alkynyl, $-X^4COOR^5$, $-X^5$-cyclloweralkyl, $-X^4NR^6R^7$, $-X^4CONR^6R^7$, $-X^4CN$, $-X^4CF_3$, hydroxy, cyano, amino, nitro, loweracylamino, halogen or lower alkoxy;

$X^2$ is

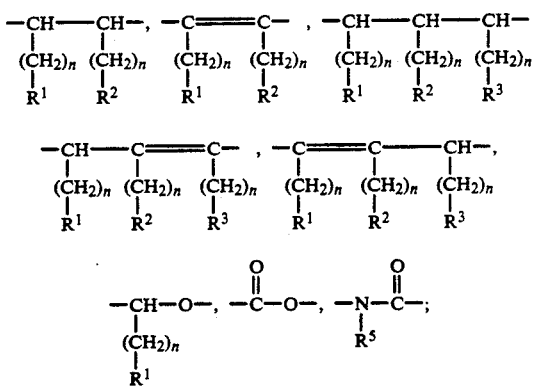

$X^3$ is $-CH_2-$, $-CH_2-CH_2-$,

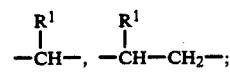

$R^1$, $R^2$ and $R^3$ are independently hydrogen, a $C_{1-6}$ linear or branch chained alkyl, 2-pyridyl, 3-pyridyl, 4-pyridyl, or a substituted or unsubstituted phenyl wherein if the phenyl is substituted there may be 1 or 2 substituents, which may be at any position on the phenyl ring and the substituents are independently halogen, $C_{1-6}$ loweralkyl, $C_{1-6}$ loweralkoxy, carboxyl, cyano, loweralkylthio, carboxyloweralkyl, nitro, —CF₃ or hydroxy;
R⁴ is

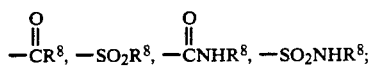

R⁵ is H, loweralkyl, cycloloweralkyl, substituted or unsubstituted phenyl, wherein if the phenyl is substituted there may be 1 or 2 substituents which may be at any position on the phenyl ring and the substituents are independently halogen, C₁₋₆ loweralkyl, C₁₋₆ loweralkoxy, nitro, or CF₃;

R⁶ and R⁷ are independently R⁵ or in combination with the N of the NR⁶R⁷ group form an unsubstituted or mono or disubstituted, saturated or unsaturated, 4-7 membered heterocyclic ring or benzofused 4-7 membered heterocyclic ring or said heterocyclic ring and said benzofused heterocyclic ring may further contain a second heteroatom selected from O and NCH₃ and the substituent(s) is/are independently selected from C₁₋₄ alkyl;

R⁸ is —(CH₂)ₙ R⁹, —(CH₂)ₙ

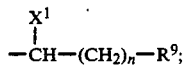

R⁹ is substituted or unsubstituted phenyl wherein the substituents may be 1 or 2 of halo, loweralkyl, loweralkoxy, loweralkylthio, carboxyl, carboxyloweralkyl, nitro, —CF₃, hydroxy; 2-pyridyl, 3-pyridyl, 4-pyridyl; C₁₋₁₅ loweralkyl, cycloloweralkyl, polycycloloweralkyl, bicycloloweralkyl, tricycloloweralkyl, any of which may contain O or N in place of one or two carbon atoms, and/or one or more double or triple bonds between adjacent carbon atoms, and any of which may be substituted or unsubstituted wherein the substituents may be independently 1 or 2 of, —OH, =O, =NOH, =NOCH₃, —NH—COCH₃,

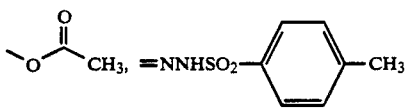

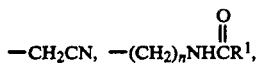

—OR¹, —NR¹₂, NHBOC, halogen, loweralkoxy, carboxy, carboalkoxy, carboxyloweralkyl, carboalkoxyloweralkyl, (CH₂)ₙNR¹₂, substituted or unsubstituted phenyl wherein the substituents may be 1 or 2 of halo, loweralkyl, loweralkoxy, loweralkylthio, carboxyl, carboxyloweralkyl, nitro, —CF₃, hydroxy;

n is 0 to 4

X⁴ is absent or C₁₋₄ alkyl;

X⁵ is absent or C₁₋₄ alkyl, O or NH;

and the pharmaceutically acceptable salts thereof.

Preferred compounds of Formula I are these wherein:

X¹ is hydrogen or halogen or C₁₋₆ linear or branch chained alkyl;

X² is —CH₂—CH₂—, —CH=CH—, —CH₂CH₂CH₂—;

X³ is —CH₂—CH₂—;

R⁴ is

R⁸ is —(CH₂)ₙR⁹;

R⁹ is substituted or unsubstituted phenyl wherein the substituents may be 1 or 2 of halo, loweralkyl, loweralkoxy, loweralkylthio, carboxyl, carboxyloweralkyl, nitro, —CF₃, hydroxy; 2-pyridyl, 3-pyridyl, 4-pyridyl; C₁₋₁₅ loweralkyl, cycloloweralkyl, polycycloloweralkyl, bicycloloweralkyl, tricycloloweralkyl, any of which may contain O or N in place of one or two carbon atoms, and/or one or more double or triple bonds between adjacent carbon atoms, and any of which may be substituted or unsubstituted wherein the substituents may be independently 1 or 2 of, —OH, =O, =NOH₄ =NOCH₃, —NH—COCH₃,

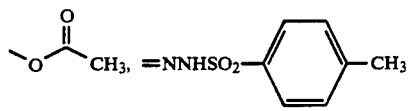

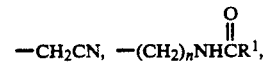

—OR¹, —NR¹₂, NHBOC, halogen, loweralkoxy, carboxy, carboalkoxy, carboxyloweralkyl, carboalkoxyloweralkyl, (CH₂)ₙNR¹₂, substituted or unsubstituted phenyl wherein the substituents may be 1 or 2 of halo, loweralkyl, loweralkoxy, loweralkylthio, carboxyl, carboxyloweralkyl, nitro, —CF₃, hydroxy;

n is 0 to 2.

As used herein, the definition of each expression, e.g. m, n, p, loweralkyl, etc., when it occurs more than once in any structure, is intended to be independent of its definition elsewhere in the same structure.

As used herein, halo is F, Cl, Br or I; loweralkyl is 1-7 carbon straight or branched chain alkyl and includes methyl, ethyl, propyl, isopropyl, butyl, isobutyl, and t-butyl, pentyl, hexyl, and heptyl; in loweralkoxy and loweralkylthio and other usages, the alkyl portion is loweralkyl as previously defined; cycloloweralkyl is cycloalkyl of 3-20 carbons and may be mono or polycyclic as, for example, in cyclohexyl, bicyclo[2,2,2]-octyl, 1- or 2-adamantyl, 7,7-dimethylbicyclo[2,2,1]heptyl; loweralkenyl is 1-7 carbon straight or branched chain alkenyl; acyl is formyl, acetyl, propionyl, benzoyl or butyryl; loweralkynyl is 1-7 carbon straight or branched chain alkynyl. Boc is t-butoxycarbonyl.

The pharmaceutically acceptable salts of the compounds of Formulas I include the conventional non-toxic salts or the quarternary ammonium salts of the compounds of Formula I formed, e.g., from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I are also readily prepared by conventional procedures such as treating an acid of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammonium hydroxide and the like.

The ability of the compounds of Formula I to antagonize oxytocin makes these compounds useful as pharmaceutical agents for mammals, especially for humans, for the treatment and prevention of disorders wherein oxytocin may be involved. Examples of such disorders include preterm labor and especially dysmenorrhea. These compounds may also find usefulness for stoppage of labor preparatory to Caesarian delivery. Because of the known relationship of vasopressin to oxytocin, the compounds of the present invention are also useful as vasopressin antagonists. They are useful in the treatment or prevention of disease states involving vasopressin disorders.

The compounds of Formula I may be administered to a human subject either alone or, preferably, in combination with pharmaceutically-acceptable carriers or diluents, optionally with known adjuvants, such as alum, in a pharmaceutical composition, according to standard pharmaceutical practice. The compounds can be administered orally or parenterally, including intravenous, intramuscular, intraperitoneal and subcutaneous.

For oral use of an antagonist of oxytocin according to this invention, the selected compounds may be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents include lactose and dried corn starch. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

When a compound according to Formula I is used as an antagonist of oxytocin in a human subject, the daily dosage will normally be determined by the prescribing physician with the dosage generally varying according to the age, weight, and response of the individual patient, as well as the severity of the patient's symptoms. However, in most instances, an effective daily dosage will be in the range of from about 0.5 mg/kg to about 50 mg/kg of body weight administered in single or divided doses. In some cases, however, it may be necessary to use dosages outside these limits.

The compounds of Formula I are prepared according to the following schemes.

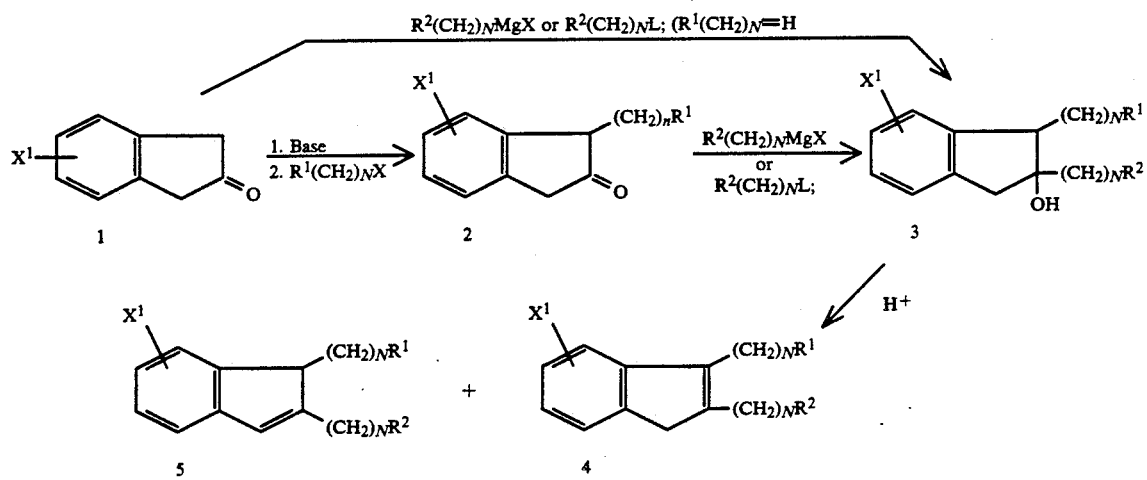

-continued
SCHEME I
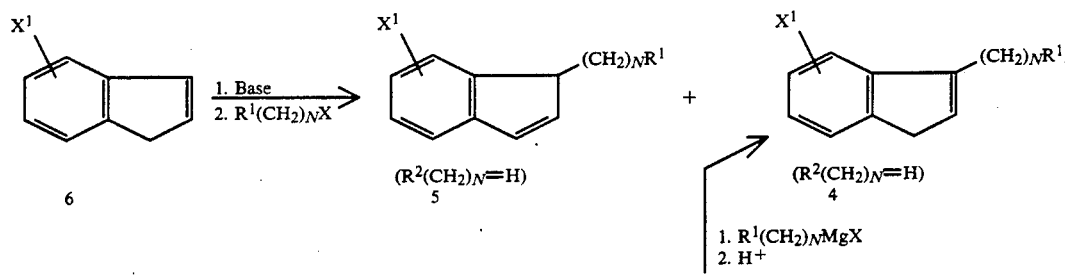
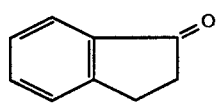
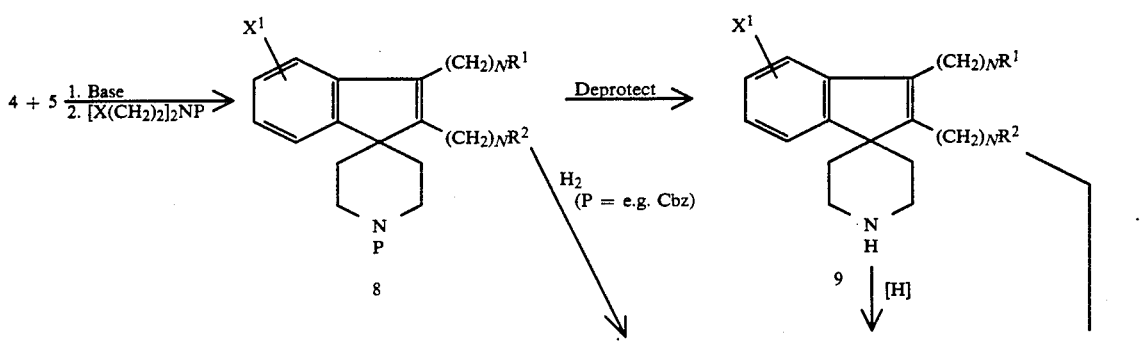
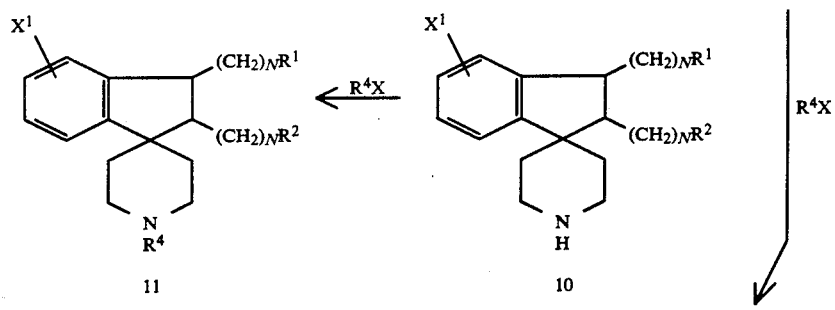
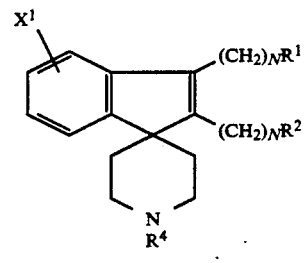

5,091,387
-continued
SCHEME I
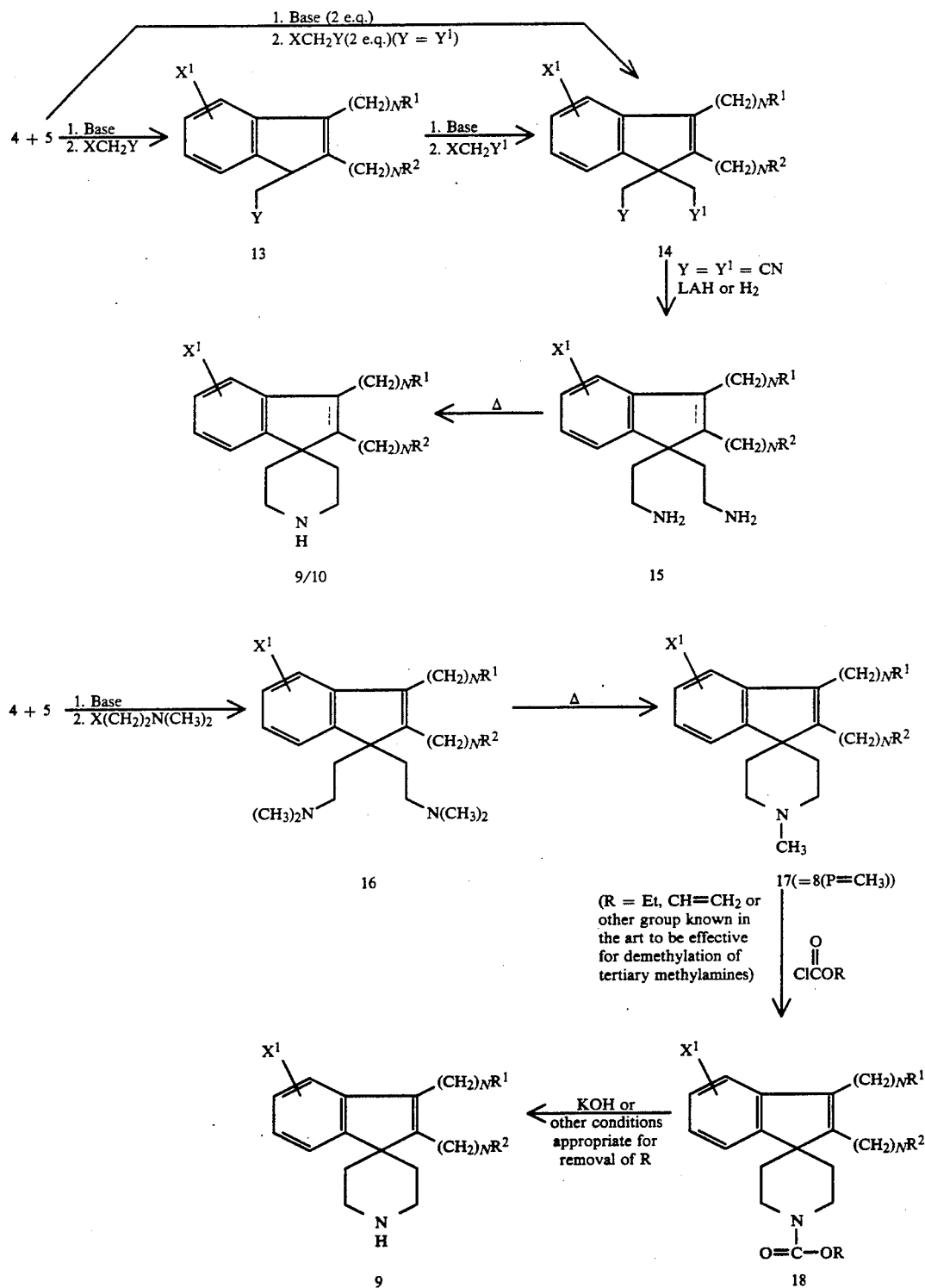

SCHEME II
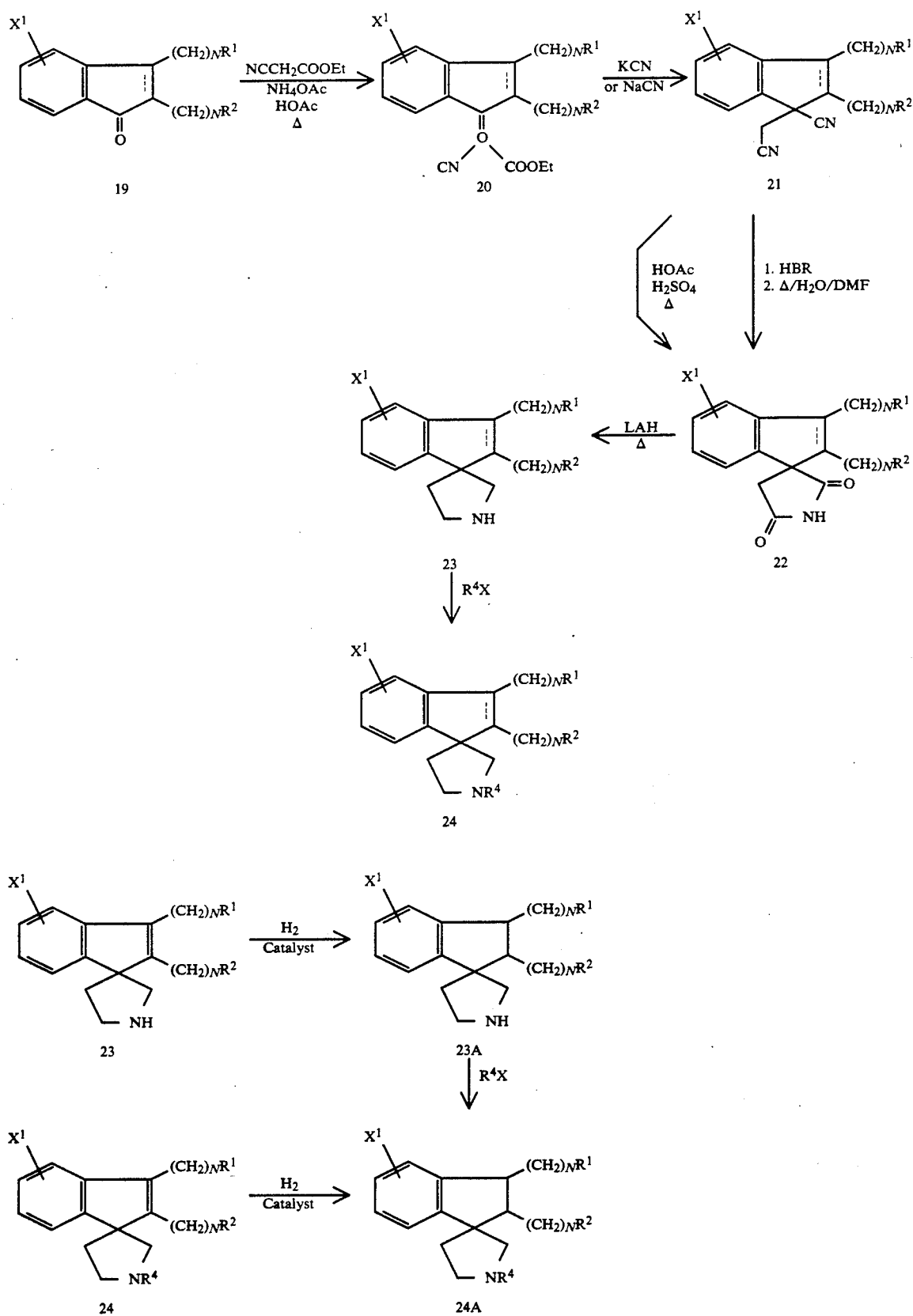

SCHEME III
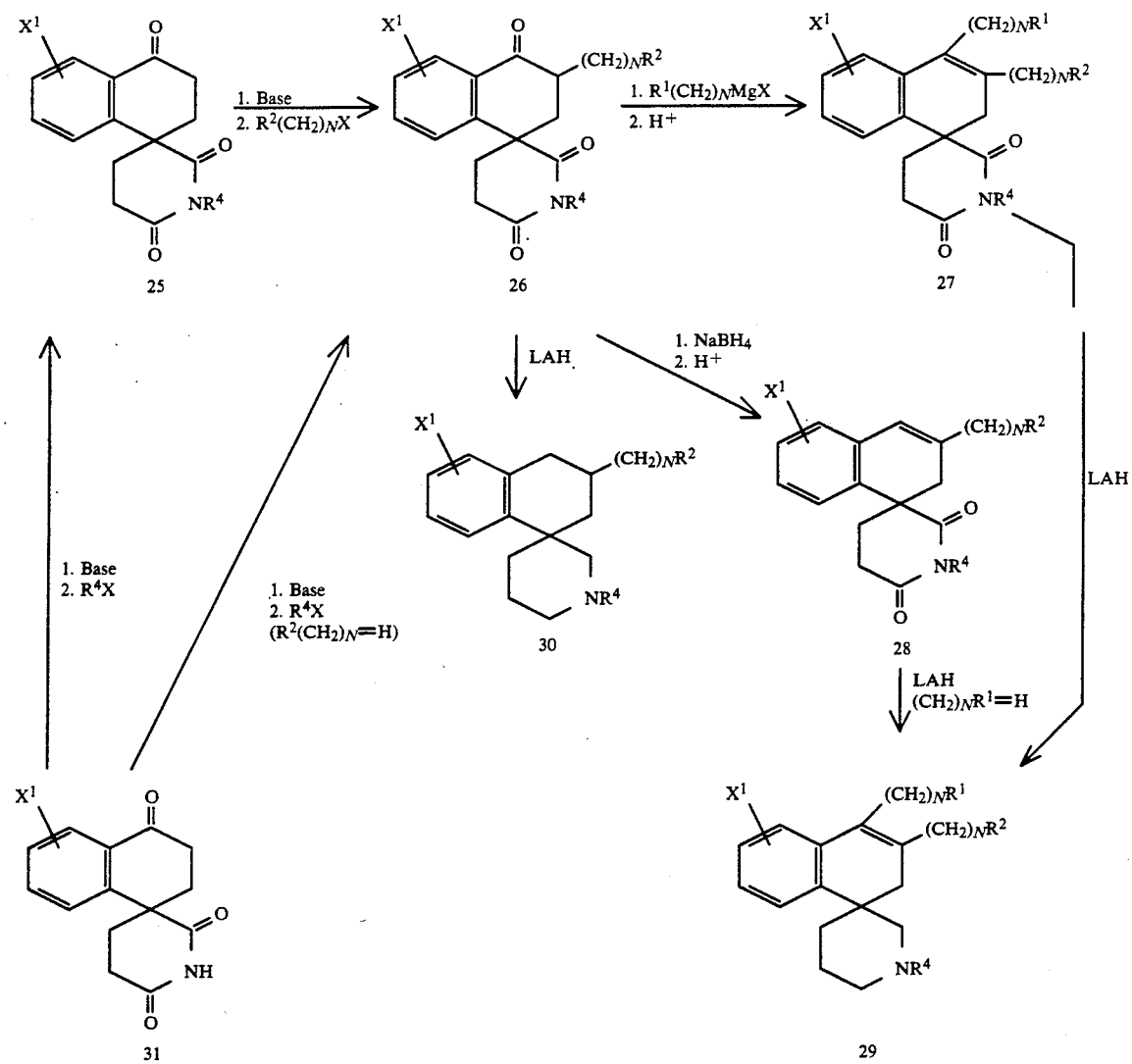
SCHEME IV
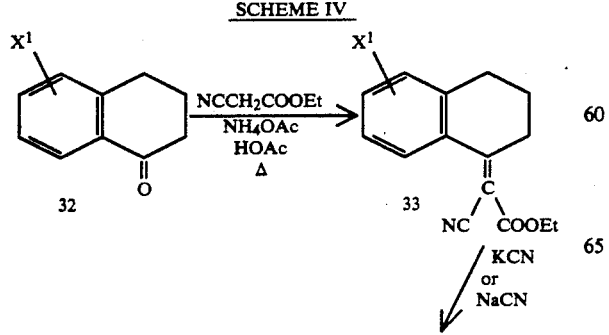
-continued
SCHEME IV
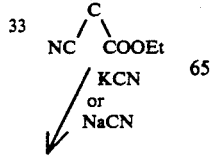

-continued
SCHEME IV

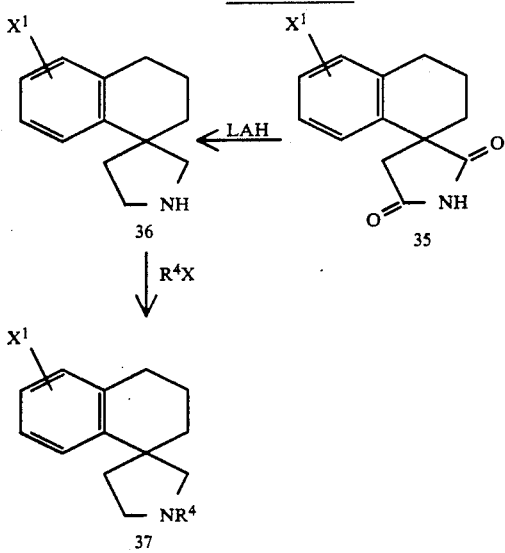

In reaction Schemes I to IV:

X is Cl, Br, OTs, etc;

P is an N-Protecting group such as BOC, Cbz, etc., or other N-Protecting groups known in the art.

The base used is LDA, KotBu, NaNH$_2$ or other strong base known in the art; the symbol ('''') may be a single or double bond depending, for example, on the conditions chosen for conversion of 14 to 15 in Scheme I; and "deprotect" as used in Scheme I is a reaction condition known in the art to be effective for removal of protecting group P.

Indenes and their 2-oxo derivatives (1) are elaborated to the spiropiperidine analogs according to Scheme I which is based on the method of Matier et al., *J. Org. Chem.*, Vol. 36, No. 5, 650–654, (1971). Specifically, indenes of structures 4 and 5 are treated with strong base, such as alkali metal amide, alkali metal alkoxides, sodium or potassium hydride, LDA, or other suitable base, followed by or in the presence of a bis(2-substituted ethyl)amine in which the 2-substituent in each ethyl chain is a suitable leaving group such as Cl, Br, I, OTs, etc. The amine generally contains a third alkyl group such as methyl or benzyl, or another protecting group such as Boc, Cbz etc. The protecting group is removable from the product 8 by methods known in the art.

A variant of the procedure, also described in Matier et al., *J. Org. Chem.*, Vol. 36, No. 5, 650–654, (1971), involves the use of for example, dimethylaminoethyl halide as the alkylating agent to convert 4 or 5, first to 13 (Y=(CH$_3$)$_2$N) and then, by repeating the alkylation, to 16. Thermal cyclization provides the piperidine 17 which is deprotected as described above to give 9. In Scheme I, 17 is treated with an alkyl chloroformate to give the dimethylated carbamate 18 which is cleaved to 9 by base hydrolysis. Reacting 9 with suitable electrophiles, such as alkyl halides, acyl halides or anhydrides, alkyl or aryl isocyanates, alkyl or aryl sulfonyl halides, gives the product 12. Reduction interspersed with these procedures at an appropriate locus provides the reduced analogs 11.

Indenes or indanes are elaborated to the spiro[indan-1,3'-pyrrolidine]-2',5'-diones 22 according to the procedure of Crooks et. al., *J. Pharm. Sci.*, Vol. 71, No. 3, 291–294 (1982). This procedure is described in Scheme II. The compounds of Scheme II are reduced to 23 as described in Crooks et. al., and reacted with electrophiles such as those used for conversion of 9 to 12, to afford products 24. Reductions may be interspersed in these syntheses as shown in Scheme II, so that both the indene and indane modifications of 24/24A may be obtained.

Tetralins 32 are similarly elaborated to spiro[tetralin-1,3'-pyrrolidines] 36 as described by Crooks et. al., *J. Med. Chem.*, 23, 679–682 (1980), and summarized in Scheme IV, and the compounds 36 are converted to 37 as described above.

Spirotetralinpiperidines such as 31 are prepared as described by Campbell, *J. Chem. Soc.*, 1377–1380 (1954). Reaction with electrophiles as described for conversion of 9 to 12 converts 31 to 25 which maybe alkylated wih base followed by alkyl or aralkyl halide or tosylate to give 26. 26 may be converted to 27 by addition of organometallic agents such as Grignard or alkyllithium reagents, and these may be reduced, such as with LAH to give 29. Alternatively, reduction of 26 as, for example, with sodium borohydride followed by dehydration, gives 28, which may be reduced with, for example, LAH to 29 (R$^2$(CH$_2$)$_N$=H). Reduction of 26 with for example, LAH gives 30.

The invention is further defined by reference to the following examples which are intended to be illustrative and not limiting.

EXAMPLE 1

Spiro(1H-indene-1,4'-piperidine)

Step 1

Di-t-butyl dicarbonate (31 g, 0.14 mole) and bis(2-chloroethyl)amine hydrochloride (21.6 g, 0.12 mole) were combined in CH$_2$Cl$_2$ (250 ml) stirred at ambient temperature and treated with triethylamine (12.8 g, 0.127 mole) added dropwise over 15 min. After 1 hr., another 1.5 ml of triethylamine was added. After a total of 2.5 hrs., the mixture was poured onto a silica gel column packed with CH$_2$Cl$_2$:hexane (1:1), and eluted with CH$_2$Cl$_2$. The combined product fractions were evaporated to dryness in vacuo to give N,N-bis(2-chloroethyl)-t-butyl-carbamate.

Step 2

To a solution of indene (10.3 g, 89 mmole) in dry tetrahydrofuran (THF, 18 ml) cooled in an ice bath and maintained under a nitrogen blanket was added lithium bis(trimethylsilyl)amide (177 ml of a 1.0M solution in THF; 177 mmole) over 15 min. The mixture was stirred in the cold for 30 min, then added over 15 min to a solution of N,N-bis(2-chloroethyl)-t-butylcarbamate (21.2 g, 88 mmole) stirred in an ice bath. The mixture was stirred for 2 hrs in the cold and for 30 min at ambient temperature under nitrogen, then evaporated in vacuo to a foam. CH$_2$Cl$_2$ was added and the resulting mixture poured onto a silica gel column packed with 40% hexane in CH$_2$Cl$_2$. The column was eluted with 40% hexane in CH$_2$Cl$_2$ followed by CH$_2$Cl$_2$, and the product fractions were evaporated to dryness in vacuo to provide 1'-(t-butyloxycarbonyl)-spiro(indene-1,4'-piperidine).

Step 3

1'-(t-Butyloxycarbonyl)spiro(indene-1,4'-piperidine) (16 g, 56 mmole) in ethyl acetate (250 ml) was stirred in an ice bath and saturated with HCl(g) for 30 min. The mixture was evaporated to dryness. Ethyl acetate was added and removed in vacuo three times, and the residue was triturated with diethyl ether and filtered to provide spiro(1H-indene-1,4'-piperidine) hydrochloride. The free base was obtained by slurrying the hydrochloride in aqueous sodium bicarbonate solution and extracting with $CH_2Cl_2$. The organic layer was separated, dried over sodium sulfate, filtered, and evaporated to dryness in vacuo to provide the title compound.

EXAMPLE 2

1'-((4-Methylphenyl)SULFONYL)SPIRO(1H-INDENE-1,4'-PIPERIDINE)

Spiro(1H-indene-1,4'-piperidine)hydrochloride (65 mg, 293 μmol) and p-toluenesulfonyl chloride (61.9 mg, 325 μmol) were combined in $CH_2Cl_2$ and treated with triethylamine (2 drops). The mixture was stirred at ambient temperature for 1 hour, then poured onto a silica gel column and eluted with 35% hexane in $CH_2Cl_2$. The product fractions were combined and evaporated to dryness in vacuo to provide the title compound which was crystallized from ether, filtered and dried in vacuo overnight at ambient temperature: (m.p. 168°-170°).
NMR: Consistent with structure.
HPLC: >99.8% pure.
MS: Molecular ion @ m/e=339.
Anal. Calc'd for $C_{20}H_{21}NO_2S$: C, 70.77; H, 6.24; N, 4.13. Found: C, 70.50; H, 6.29; N, 4.10.

EXAMPLE 3

1'-((4-Bromophenyl)SULFONYL)SPIRO(1H-INDENE-1,4'-PIPERIDINE)

Spiro(1H-indene-1,4'-piperidine) (15 mg, 81.1 μmol) and p-bromobenzenesulfonyl chloride (21 mg, 81.1 μmol) were combined in $CH_2Cl_2$ and treated with triethylamine (2 drops). The mixture was stirred at ambient temperature for 15 min, then poured onto a silica gel column and eluted with 1:1 $CH_2Cl_2$: hexane. The product fractions were combined and evaporated to dryness in vacuo to provide the title compound as a solid which was dried in vacuo overnight at ambient temperature: (m.p. 177°-178°).
TLC: $R_f$=0.71 Silica gel ($CH_2Cl_2$).
NMR: Consistent with structure.
HPLC: >96.9% pure.
MS: Molecular ion @ m/e=403.
Anal. Calc'd for $C_{19}H_{18}BrNO_2S$: C, 56.44; H, 4.49; N, 3.46. Found: C, 56.10; H, 4.35; N, 3.37.

EXAMPLE 4

1'-((4-Methoxyphenyl)SULFONYL)SPIRO-(1H-INDENE-1,4'-PIPERIDINE)

The procedure of example 3 was carried out using 20 mg (0.108 mmol) of spiro(1H-indene-1,4'-piperidine), and substituting p-methoxybenzenesulfonyl chloride (21 mg, 0.1 mmol) for the p-bromo derivative. The title compound was obtained as a solid: (m.p. 181°-183°).
TLC: $R_f$=0.49 Silica gel ($CH_2Cl_2$).
NMR: Consistent with structure.
HPLC: >99.0% pure.
MS: M+H @ m/e=356 (FAB).
Anal. Calc'd for $C_{20}H_{21}NO_3S$: C, 67.58; H, 5.95; N, 3.94. Found: C, 67.42; H, 5.88; N, 3.88.

EXAMPLE 5

2-(Spiro(1H-indene-1,4'-piperidin)-1'-ylsulfonyl)-benzoic acid methyl ester

The procedure of example 3 was carried out using 20 mg (0.108 mmol) of spiro(1H-indene-1,4'-piperidine), and substituting o-methoxy-carbonylbenzenesulfonyl chloride (23.5 mg, 0.1 mmol) for the p-bromo derivative. Chromatographic elution was with 2:1 $CH_2Cl_2$:hexane. The title compound was obtained as a solid which was recrystallized from petroleum ether and dried in vacuo overnight: (m.p. 150°-152°).
TLC: $R_f$=0.25 Silica gel ($CH_2Cl_2$).
NMR: Consistent with structure, hexane observed.
HPLC: >99.0% pure.
MS: M+H @ m/e=384 (FAB).
Anal. Calc'd for $C_{21}H_{21}NO_4S \cdot 0.82$ hexane: C, 68.55; H, 7.21; N, 3.08. Found: C, 68.73; H, 6.61; N, 3.01.

EXAMPLE 6

(1S)-1'-(((7,7-Dimethyl-2-oxobicicylo-(2.2.1)hept-1-yl)-methyl)sulfonyl)spiro(1H-indene-1,4'-piperidine)

The procedure of example 3 was carried out using 308 mg (1.66 mmol) of spiro(1H-indene-1,4'-piperidine) and 0.23 ml (1.66 mmol) of triethylamine, and substituting (+)-10-camphorsulfonyl chloride (418 mg, 1.66 mmol) for p-bromobenzenesulfonyl chloride. Chromatographic elution was with $CH_2Cl_2$. The title compound was obtained as a solid which was recrystallized from petroleum ether and dried overnight in vacuo at ambient temperature: (m.p. 148°-149°).
TLC: $R_f$=0.44 Silica gel ($CH_2Cl_2$).
NMR: Consistent with structure.
HPLC: >99.6% pure.
MS: Molecular ion @ m/e=399.
Anal. Calc'd for $C_{23}H_{29}NO_3S$: C, 69.14; H, 7.32; N, 3.51. Found: C, 68.99; H, 7.44; N, 3.50.

EXAMPLE 7

(1R)-1'-(((7,7-Dimethyl-2-oxobicicylo-(2.2.1)hept-1yl)-methyl) sulfonyl)spiro-(1H-indene- 1,4'-piperidine)

The procedure of example 3 was carried out using 20 mg (0.108 mmol) of spiro (1H-indene-1,4'-piperidine), and substituting (−)-10-camphorsulfonyl chloride (25 mg, 0.100 mmol) for p-bromobenzenesulfonyl chloride. Chromatographic elution was with 7:3 $CH_2Cl_2$:hexane. The title compound was obtained as a solid which was recrystallized from petroleum ether and dried 6 hrs in vacuo at ambient temperature: (m.p. 146°-147°).
TLC: $R_f$=0.44 Silica gel ($CH_2Cl_2$).
NMR: Consistent with structure.
HPLC: >99.7% pure
MS: Molecular ion @ m/e=399.
Anal. Calc'd for $C_{23}H_{29}NO_3S$: C, 69.14; H, 7.32; N, 3.51. Found: C, 68.97; H, 7.24; N, 3.38.

EXAMPLE 8

N-Tricyclo(3.3.1.1 (3,7))dec-2-yl-spiro(1H-indene-1,4'-piperidine)-1'-carboxamide Spiro(1H-indene-1,4'-piperidine) (20 mg, 0.108 mmol) and 2-adamantyl isocyanate (18 mg, 0.10 mmol) were combined in $CH_2Cl_2$ and stirred overnight at ambient temperature. An additional 5 mg (0.028 mmol) of 2-adamantyl isocyanate and 2 drops of triethylamine were added and the mixture again stirred overnight at ambient temperature. The mixture was chromatographed directly on a silica gel column eluted with $CH_2Cl_2$ followed by 0.5% and 1% methanol in $CH_2Cl_2$. The product fractions were combined and evaporated to dryness in vacuo, and the residue was crystallized from petroleum ether to provide the title compound as a solid: (mp 189°–191°).

TLC: $R_f=0.34$ Silica gel (2% $CH_3OH$ in $CH_2Cl_2$).
NMR: Consistent with structure.
HPLC: >99.7% pure
MS: Molecular ion @ m/e=362.
Anal. Calc'd for $C_{24}H_{30}N_2O$: C, 79.52; H, 8.34; N, 7.73. Found: C, 79.64; H, 8.33; N, 7.64.

EXAMPLE 9

(1S)-1'-(((2-Hydroxy-7,7-dimethylbicyclo-(2.2.1)hept-1-yl)methyl)sulfonyl)spiro(1H-indene-1,4'-piperidine), exo isomer (compound A) and endo isomer (compound B)

Lithium aluminum hydride solution (360 μl of 1.0M in THF; 0.36 mmol) was diluted with dry THF (2 ml) and heated at reflux under nitrogen. A solution of (1S)-1'-(((7,7-dimethyl-2-oxobicicylo(2.2.1)hept-1-yl) methyl)sulfonyl)spiro(1H-indene-1,4'-piperidine) (120 mg, 0.30 mmol) in THF (3 ml) was added dropwise over 30 min. The reaction was heated at reflux for another 3 hr, then maintained at 50° overnight. The reaction was diluted with ether (50 ml), washed first with 1M HCl then with saturated sodium bicarbonate solution, dried over sodium sulfate, filtered, and evaporated to dryness in vacuo. The residue was chromatographed on a silica gel column and eluted with $CH_2Cl_2$ to give compound A. Further elution with 2% MeOH in $CH_2Cl_2$ gave crude compound B which was rechromatographed on a silica gel column eluted with 0.5% MeOH in $CH_2Cl_2$ to give pure compound B.

Compound A: The fractions containing compound A were evaporated to dryness in vacuo and the residue crystallized from ether. The solid obtained was dried in vacuo for 2 hrs at ambient temperature: (mp 167°–169°).
TLC: $R_f=0.36$ Silica gel ($CH_2Cl_2$).
NMR: Consistent with structure.
HPLC: >99.3% pure
MS: Molecular ion @ m/e=401.
Anal. Calc'd for $C_{23}H_{31}NO_3S$: C, 68.79; H, 7.78; N, 3.49. Found: C, 68.96; H, 7.96; N, 3.50.

Compound B: The fractions containing compound B were evaporated to dryness in vacuo and the residue crystallized from ether. The solid obtained was dried in vacuo overnight: (mp 175°–177°).
TLC: $R_f=0.21$ Silica gel ($CH_2Cl_2$).
NMR: Consistent with structure.
HPLC: >99.4% pure
MS: Molecular ion m/e=401.
Anal. Calc'd for $C_{23}H_{31}NO_3S$: C, 68.79; H, 7.78; N, 3.49. Found: C, 68.63; H, 7.82; N, 3.48.

EXAMPLE 10

(1R)-1'-(((2-Hydroxy-7,7-dimethylbicyclo-(2.2.1)hept-1-yl)methyl)sulfonyl)spiro(1H-indene-1,4'-piperidine), exo isomer (compound A) and endo isomer (compound B)

The procedure of example 9 was carried out using (1R)-1'-(((7,7-dimethyl-2-oxobicicylo-(2.2.1)-hept-1-yl)methyl)sulfonyl)spiro(1H-indene-1,4'-piperidine) in place of the (1S) isomer. The evaporated residues from compounds A and B were each crystallized from petroleum ether and dried overnight in vacuo.

Compound A: (mp 166°–168°).
TLC: $R_f=0.35$ Silica gel ($CH_2Cl_2$).
NMR: Consistent with structure, hexane observed.
HPLC: >99.0% pure
MS: Molecular ion @ m/e=401.
Anal. Calc'd for $C_{23}H_{31}NO_3S \cdot 0.15$ hexane: C, 69.26; H, 8.05; N, 3.38. Found: C, 69.46; H, 7.98; N, 3.24.

Compound B: (mp 172°–175°).
TLC: $R_f=0.19$ Silica gel ($CH_2Cl_2$).
NMR: Consistent with structure.
HPLC: >91.6% pure
MS: Molecular ion @ m/e=401.
Anal. Calc'd for $C_{23}H_{31}NO_3S$: C, 68.79; H, 7.78; N, 3.49. Found: C, 69.04; H, 7.88; N, 3.44.

EXAMPLE 11

(1S)-1'-(((2-Hydroxy-7,7-dimethyl-2-phenyl-bicyclo(2.2.1)hept-1-yl)methyl)sulfonyl)spiro(1H-indene-1,4'-piperidine)

The procedure of example 13 was carried out using phenylmagnesium bromide (165 μl of a 3.0M solution in ether; 0.50 mmol) in place of methylmagnesium bromide. The chromatographed product was crystallized from petroleum ether and dried in vacuo for 2 hrs: (mp 159°–160°).

TLC: $R_f=0.31$ Silica gel (15% EtOAc in $CH_2Cl_2$).
NMR: Consistent with structure, hexane observed.
HPLC: >91.7% pure
MS: Molecular ion not observed; $M-H_2O$ @ m/e=459.
Anal. Calc'd for $C_{29}H_{35}NO_3S \cdot 0.10$ hexane: C, 70.49; H, 7.68; N, 2.78. Found: C, 70.45; H, 7.63; N, 2.55.

EXAMPLE 12

(1S)-1'-((4,7,7-Trimethyl-3-oxo-2-oxabicyclo-(2.2.1)hept-1-yl)carbonyl)spiro(1H-indene-1,4'-piperidine)

Spiro(1H-indene-1,4'-piperidine) (40 mg, 0.216 mmol) and (1S)-(−)-camphanic acid chloride (47 mg, 0.216 mmol) were combined in $CH_2Cl_2$ and treated with triethylamine (2 drops). The mixture was stirred at ambient temperature for 15 min, then evaporated to dryness in vacuo. The residue was chromatographed on a silica gel column eluted with $CH_2Cl_2$. The product fractions were combined and evaporated to dryness in vacuo. The residue was crystallized from petroleum ether, and the resulting solid dried in vacuo at ambient temperature overnight to give the title compound: (mp 215°–216°).

TLC: $R_f=0.44$ Silica gel ($CH_2Cl_2$).
NMR: Consistent with structure, hexane observed.
HPLC: >96.9% pure
MS: Molecular ion observed @ m/e=365.
Anal. Calc'd for $C_{23}H_{27}NO_3 \cdot 0.15$ hexane: C, 75.86; H, 7.75; N, 3.70. Found: C, 75.91; H, 7.76; N, 3.70.

EXAMPLE 13

Exo-(1S)-1'-(((2-hydroxy-2,7,7-trimethylbicyclo-(2.2.1)hept-1-yl)methyl)sulfonyl)spiro(1H-indene-1,4'-piperidine)

(1S)-1'-(((7,7-Dimethyl-2-oxobicyclo(2.2.1)-hept-1-yl)methyl)sulfonyl)spiro(1H-indene-1,4'-piperidine) (55 mg, 0.138 mmol) was dissolved in ether and stirred under nitrogen in an ice bath. Methylmagnesium bromide (230 μl of a 3.0M solution in ether; 0.69 mmol) was added, and the mixture stirred 2 hrs in the cold and overnight at ambient temperature. Water was added followed by 1M HCl, and the mixture was extracted with ether. The ether layers were washed with aqueous sodium bicarbonate, dried over sodium sulfate, filtered, and evaporated to dryness in vacuo. The residue was chromatographed on a silica gel column eluted with 10% ethyl acetate in hexane. The product fractions were combined and evaporated to dryness in vacuo, and the residue crystallized from petroleum ether to give the title compound as a solid which was dried in vacuo for 2 hrs: (mp 161°–162°).

TLC: $R_f$=0.33 Silica gel (15% EtOAc in hexane).
NMR: Consistent with structure.
HPLC: >99.8% pure
MS: Molecular ion @ m/e=415.
Anal. Calc'd for $C_{24}H_{33}NO_3S$: C, 69.36; H, 8.00; N, 3.37. Found: C, 69.44; H, 8.11; N, 3.32.

EXAMPLE 14

N-(2-(2,3-Dihydro-1H-inden-1-yl)ethyl)-7,7-dimethyl-2-oxo-bicyclo(2.2.1)heptane-1-methanesulfonamide Indene (2 ml), 1.99 g, 17.2 mmol) was dissolved in dry THF (2 ml) and stirred at −78° under nitrogen. n-Butyllithium (6.87 ml of a 2.5M solution in hexane: 17.2 mmol) was added, and the solution was then warmed to ambient temperature, stirred for 15 minutes, recooled to −78°, and added via syringe to a solution of chloroacetonitrile (1.09 ml, 1.30 g, 17.2 mmol) in THF (2 ml) stirred at −78°. After completion of the addition, the solution was diluted with ether (200 ml) and washed with 1M HCl followed by saturated sodium bicarbonate solution. The ether layer was dried over sodium sulfate, filtered, and evaporated to dryness in vacuo. The residue was chromatographed on a silica gel column eluted with 10% EtOAc in hexane and the product fractions evaporated in vacuo to give 3-cyanomethylindene. 3-Cyanomethylindene (310 mg, 2.0 mmol) was dissolved in a 10% solution of conc. ammonium hydroxide in absolute ethanol. 5% Rhodium/alumina catalyst (60 mg) was added and the mixture was shaken under an atmosphere of hydrogen (40 psi) overnight. The mixture was filtered, and the filtrate was evaporated to dryness in vacuo. The residue was chromatographed on a silica gel column eluted with 93:7:0.7 $CH_2Cl_2$:MeOH:$NH_4OH$, and the product fractions were combined and evaporated to dryness in vacuo to provide 1-(2-aminoethyl)indane. 1-(2-Aminoethyl)indane (47 mg, 0.292 mmol) and (+)-10-camphorsulfonyl chloride (73 mg, 0.29 mmol) were combined in $CH_2Cl_2$ (2 ml), treated with triethylamine (2 drops), and stirred at ambient temperature overnight. The mixture was evaporated to dryness in vacuo and the residue chromatographed on a silica gel column eluted in with 20% EtOAc in hexane. The product fractions were combined and evaporated to dryness in vacuo. The resulting oil was dried in vacuo at ambient temperature for 3 hours to provide the title compound as a solid: (mp 52°–70°).

TLC: $R_f$=0.43 Silica gel (30% EtOAc in hexane)
NMR: Consistent with structure, $CH_2Cl_2$ observed.
HPLC: >98.7% pure
MS: Molecular ion @ m/e=375.
Anal: Calc'd for $C_{21}H_{29}NO_3S$•0.05$CH_2Cl_2$: C, 66.57; H, 7.72; N, 3.69. Found: C, 66.63; H, 7.69; N, 3.58.

EXAMPLE 15

(1S)-1'-(((2-Ethyl-2-HYDROXY-7,7-DIMETHYL-BICYCLO(2.2.1)HEPT-1-YL)METHYL)SULFONYL)SPIRO(1H-INDENE-1,4'-PIPERIDINE)

The procedure of example 13 was carried out using ethylmagnesium bromide (175 ml of a 3.85M solution in ether; 0.67 mmol) in place of methylmagnesium bromide. Chromatography on a silica gel column (10% EtOAc in hexane) separated the product from several contaminants which included the starting ketone and the carbinol, exo-(1S)-1'-(((2-hydroxy-7,7-dimethyl-bicyclo(2.2.1)hept-1-yl)-methyl)sulfonyl)spiro(1H-indene-1,4'-piperidine). The product fraction was evaporated to dryness in vacuo, and the residue crystallized from petroleum ether. The resulting solid was dried in vacuo at ambient temperature overnight: (mp 171°–173°).

TLC: $R_f$=0.40 Silica gel (15% EtOAc in hexane).
NMR: Consistent with structure.
HPLC: >98.2% pure
MS: Molecular ion @ m/e=459.
Anal. Calc'd for $C_{25}H_{35}NO_3S$: C, 69.89; H, 8.21; N, 3.26. Found: C, 70.07; H, 8.34; N, 3.14.

EXAMPLE 16

Exo-N-(2-(2,3-dihydro-1H-inden-1-yl)ethyl)-2-hydroxy-7,7-dimethylbicyclo(2.2.1)heptane-1-methanesulfonamide N-(2-(2,3-Dihydro-1H-inden-1-yl)ethyl)-7,7-dimethyl-2-oxo-bicyclo(2.2.1)heptane-1-methanesulfonamide (35 mg, 0.093 mmol), prepared as in example 14, was dissolved in THF (2 ml) and stirred under nitrogen at ambient temperature. Lithium aluminum hydide (93 μl of a 1.0M solution in THF; 0.093 mmol) was added and the solution stirred 2 hours at ambient temperature. 1M HCl was added and the mixture extracted with ether. The ether layer was dried over sodium sulfate, filtered, and evaporated to dryness in vacuo. The residue was chromatographed on a silica gel column eluted with 20% EtOAc in hexane. The product fractions were combined and evaporated to dryness in vacuo. The residue was triturated with petroleum ether and with $CH_2Cl_2$ and evaporated each time. The solid was dried in vacuo at ambient temperature for 72 hours.

TLC: $R_f$=0.56 Silica gel (30% EtOAc in hexane).
NMR: Consistent with structure, $CH_2Cl_2$ and hexane observed.
HPLC: >89.5% pure
MS: Molecular ion @m/e=377.
Anal. Cal'd for $C_{21}H_{31}NO_3S$•0.05$CH_2Cl_2$•0.50hexane: C, 67.98; H, 9.04; N, 3.30. Found: C, 68.03; H, 8.97; N, 3.10.

EXAMPLE 17

Exo-N-(2-(1H-inden-1-yl)ethyl)-2-hydroxy-7,7-dimethylbicyclo(2.2.1)heptane-1-methanesulfonamide 3-Cyanomethylindene (3.84 g, 0.025 mol), prepared as described in example 14, was dissolved in a mixture of hexane and THF and stirred under nitrogen at −78°. Dissobutylaluminum hydride (DIBAL) (19.2 ml of a 1.5M solution in toluene; 0.029 mmol) was added and the mixture stirred at ambient temperature 2.5 hours. Saturated sodium chloride solution (220 ml) was added and the mixture stirred another 20 minutes. 5% $H_2SO_4$ (90 ml) was added and the solution immediately extracted with ether. The ether layer was dried over sodium sulfate, filtered, and evaporated to dryness in vacuo. The residue was chromatographed on a silica gel column eluted with 8% Et$_2$O in hexane. The product fraction was evaporated to dryness to provide 2-(1H-indene-1-yl)acetaldehyde.

2-(1H-indene-1-yl)acetaldehyde (1.5 g, 9.5 mmol), hydroxylamine hydrochloride (836 mg, 12.0 mmol), and sodium acetate (1.04 g, 12.7 mmol) were combined in methanol (50 ml) and stirred at ambient temperature overnight. The mixture was evaporated to dryness in vacuo and the residue treated with water and extracted with ether. The ether layer was washed with water, dried over sodium sulfate, filtered, and evaporated to dryness in vacuo. The residue was chromatographed on a silica gel coulmn eluted with 15% EtOAc in hexane followed by 22% EtOAc in hexane. The product fraction was evaporated to dryness in vacuo to provide 2-(1H-indene-1-yl)acetaldoxime.

2-(1H-indene-1-yl)acetaldoxime (50 mg, 0.29 mmol) was dissolved in methanol (15 ml) and treated with sodium cyanoborohydride (34 mg, 0.54 mmol). Methyl orange indicator (ca 1 mg) was added, and the pH of the mixture adjusted by addition of 1:1 conc. HCl:MeOH to maintain the indicator color slightly to the red side of the turning point. After ca 1 ml of the acid mixture had been added, the indicator remained red. The reaction was made basic with conc. NH$_4$OH, and water was added. The mixture was extracted with ether and the ether layer was dried over sodium sulfate, filtered, and evaporated to dryness in vacuo to provide N-(2-(1H-indene-1-yl)-ethyl)hydroxylamine.

N-(2-(1H-Indene-1-yl)ethyl)hydroxylamine (85 mg, 0.486 mmol) was added to a slurry of zinc dust (104 mg, 1.59 mmol) in glacial acetic acid (3 ml), and the mixture was heated at 65° for 2 hours. The mixture was cooled and filtered, then made basic with conc. ammonium hydroxide and extracted with ether. The ether layer was washed with water, then with brine, dried ober sodium sulfate, filtered, and evaporated to dryness in vacuo. The residue was chromatographed on a silica gel column eluted with 90:10:1 of CH$_2$Cl$_2$:MeOH:NH$_4$OH. The product fractions were evaporated to dryness in vacuo to give (2-(1H-indene-3-yl)ethyl)amine.

(2-(1H-Indene-1-yl)ethyl)amine (190 mg, 1.19 mmol) and (+)-10-camphorsulfonyl chloride (299 mg, 1.19 mmol) were combined in CH$_2$Cl$_2$ (2 ml), treated with triethylamine (87 µl, 120 mg, 1.19 mmol), and the mixture was stirred at ambient temperature overnight. The mixture was chromatographed on a silica gel column eluted with 25% EtOAc in hexane and the product fractions were evaporated to dryness in vacuo to give N-(2-(1H-inden-3-yl)ethyl)-7,7-dimethyl-2-oxobicyclo(2.2.1)heptane-1-methanesulfonamide.

N-(2-(1H-Idene-3-yl)ethyl)-7,7-dimethyl-2-oxobicyclo(2.2.1)heptane-1-methanesulfonamide (110 mg, 0.295 mmol) was dissolved in THF (2 ml) and stirred at ambient temperature under nitrogen. Lithium aluminum hydride (590 µl of a 1.0M solution in THF; 0.59 mmol) was added and the mixture stirred 2 hours at ambient temperature. The reaction was quenched by the addition of 1M HCl followed by water, then extracted with ether. The ether layer was washed with water, dried over sodium sulfate, filtered, and evaporated to dryness in vacuo. The residue was chromatographed on a silica gel column eluted with 15% EtOAc in hexane followed by 25% EtOAc in hexane. The product fractions were evaporated to dryness in vacuo and the residue was dried in vacuo at ambient temperature for 3 hours.

TLC: Rf=0.51 Silica gel (30% EtOAc in hexane).

NMR: Consistent with structure, CH$_2$Cl$_2$ observed.

HPLC: >82.2% pure after three days (slowly decomposes).

MS: Molecular ion @ m/e=375.

Anal. Calc'd for C$_{21}$H$_{29}$NO$_3$S•0.10CH$_2$Cl$_2$: C, 65.99; H, 7.66; N, 3.65. Found: C, 66.22; H, 7.78; N, 3.54.

EXAMPLE 18

(1S(1.Alpha.,2.alpha.,4.alpha.))-2-hydroxy-7,7-dimethyl-1-((spiro(1H-indene-1,4'-piperidin)-1'-ylsulfonyl)methyl)bicyclo(2.2.1)heptane-2-acetic acid ethyl ester Lithium bis(trimethylsilyl)amide (16 ml of a 1.0M solution in THF; 16 mmole) was stirred under nitrogen at −78°. Ethyl acetate (1.5 ml, 1.35 g, 15.3 mmol) was added over 30 sec and the mixture was stirred in the cold for 15 min. A solution of (1S)-1'-(((7,7-dimethyl-2-oxobicicylo(2.2.1)hept-1-yl)methyl)sulfonyl)spiro(1H-indene-1,4'-piperidine) (3.0 g, 7.5 mmol; prepared as in example 6) in THF (20 ml) was added over 2 min to the cold mixture, and the reaction stirred in the cold another 10 min. 6N HCl (6 ml) was added rapidly, and the mixture stirred and warmed to ambient temperature. Water (20 ml) was added, the layers separated, and the water layer extracted with ether. The combined organic layers were dried over sodium sulfate, filtered, and evaporated to dryness in vacuo. The residue was chromatographed on a silica gel column eluted with 15% EtOAc in hexane. The product fractions were evaporated to dryness in vacuo to give the title compound.

EXAMPLE 19

(1S(1.Alpha.,2.alpha.,4.alpha.))-2-hydroxy-7,7-dimethyl-1-((spiro(1H-indene-1,4'-piperidin)-1'-ylsulfonyl)methyl)bicyclo(2.2.1)heptane-2-acetic acid methyl ester (1S(1.Alpha.,2.alpha.,4.alpha.))-2-hydroxy-7,7-dimethyl-1-((spiro(1H-indene-1,4'-piperidin)-1'-yl sulfonyl)methyl)bicyclo(2.2.1)heptane-2-acetic acid ethyl ester (45 mg, 0.092 mmol) was stirred in a mixture of methanol (1 ml) and water (1 ml) and treated with sodium hxdroxide (0.1 ml of a 5N solution in water; 0.5 mmol). The mixture was stirred for 1 hr at ambient temperature, then evaporated to dryness in vacuo. The residue was treated with saturated sodium bicarbonate solution and extracted with ether. The ether layer was evaporated to dryness in vacuo and the residue was chromatographed on a silica gel column eluted with 15% EtOAc in hexane. The product fractions were evaporated to dryness in vacuo, and the residue was triturated with CH$_2$Cl$_2$ and again evaporated to dryness. The residue was dried in vacuo at ambient temperature overnight to give the title compound: (mp 81°-83°).

TLC: R$_f$=0.26 Silica gel (15% EtOAc in hexane).

NMR: Consistent with structure, CH$_2$Cl$_2$ observed.

HPLC: >98.5% pure.

MS: Molecular ion ǀ m/e=473.

Anal. Calc'd for C$_{26}$H$_{35}$NO$_5$S.0.10CH$_2$Cl$_2$: C, 65.02; H, 7.36; N, 2.91. Found: C, 64.91; H, 7.44; N, 2.81.

EXAMPLE 20

(1S(1.Alpha.,2.alpha.,4.alpha.))-2-hydroxy-7,7-dimethyl-1-((spiro(1H-indene-1,4'-piperidin)-1'-ylsulfonyl)methyl)-bicyclo(2.2.1)heptane-2-acetic acid (1S(1.Alpha.,2.alpha.,4.alpha.))-2-hydroxy-7,7-dimethyl-1-((spiro(1H-indene-1,4'-piperidin)-1'-yl sulfonyl)methyl)bicyclo(2.2.1)heptane-2-acetic acid ethyl ester (3.8 g, 7.8 mmol) was stirred in methanol (40 ml) containing sodium hydroxide (10 ml of a 1.0M solution in water; 10 mmol) for 4.5 hrs. The mixture was evaporated to dryness in vacuo, treated with water (250 ml) and washed with ether. The aqueous layer was acidified with conc HCl and extracted with ether, and the ether layer from this extraction was dried over sodium sulfate, filtered, and evaporated to dryness in vacuo. The residue was chromatographed an a silica gel column eluted with $CH_2Cl_2$ followed by 90:10:0.1:0.1 of $CH_2Cl_2$:MeOH:HOAc:$H_2O$. The product fractions were evaporated to dryness in vacuo, and the residue was triturated with ether and hexane and filtered to give the title compound as a solid: (mp 137.5°–139.5°).

TLC: $R_f$=0.43 Silica gel (5% MeOH in $CH_2Cl_2$).
NMR: Consistent with structure.
HPLC: >95% pure.
MS: Molecular ion not observed.
Anal. Calc'd for $C_{25}H_{33}NO_5S$: C, 65.33; H, 7.24; N, 3.05. Found: C, 65.13; H, 7.35; N, 2.99.

EXAMPLE 21

Exo-(1S-(1.Alpha.,2.alpha.,4.alpha.))-2,3-dihydro-1'-(((2-hydroxy-7,7-dimethylbicyclo(2.2.1)hept-1-YL)-methyl)sulfonyl)spiro(1H-indene-1,4'-piperidine)

Exo-(1S)-1'-(((2-hydroxy-7,7-dimethylbicyclo-(2.2.1)hept-1-yl)methyl)sulfonyl)spiro(1H-indene-1,4'-piperidine), prepared in example 9 (compound A) (100 mg, 0.25 mmol) and 10% Palladium/carbon (10 mg) were combined in absolute ethanol (1 ml) and shaken overnight under an atmosphere of hydrogen (50 psi). The mixture was filtered and the filtrate evaporated to dryness in vacuo. The residue was chromatographed on a silica gel column eluted with 40% $Et_2O$ in hexane. The product fractions were evaporated to dryness in vacuo and the residue triturated with petroleum ether. The resulting solid was dried in vacuo at ambient temperature overnight: (mp 163°–165°).

TLC: $R_f$=0.35 Silica gel (15% EtOAc in hexane).
NMR: Consistent with structure, hexane observed.
HPLC: >94.4% pure.
MS: Molecular ion observed @ m/e=403.
Anal. Calc'd for $C_{23}H_{33}NO_3S$: C, 68.77; H, 8.41; N, 3.40. Found: C, 68.94; H, 8.30; N, 3.43.

EXAMPLE 22

1'-(((2-Oxo-1,7,7-trimethylbicicylo(2.2.1)-hept-3-yl)-methyl)carbonyl)spiro(1H-indene-1,4'-piperidine)

Spiro(1H-indene-1,4'-piperidine) (60 mg, 0.27 mmol) was dissolved in freshly degassed dimethylformamide (DMF) and treated with (+)-camphoracetic acid (62.6 mg, 0.298 mmol), 1-hydroxybenzotriazole hydrate (HBT; 40.2 mg, 0.298 mmol), and 1-ethyl-3-(3-dimethylamino-propyl)carbodiimide hydrochloride (EDC; 57.1 mg, 0.298 mmol). The pH of the solution was adjusted to 9.5 with triethylamine (60 µl) and the reaction stirred at ambient temperature for 1 hr. The DMF was removed in vacuo and the residue was treated with water, made strongly basic with saturated sodium carbonate solution, and extracted with ethyl acetate. The organic layer was washed with brine, dried over sodium sulfate, filtered, and evaporated to dryness in vacuo. The residue was chromatographed on a silica gel column eluted with 10% $Et_2O$ in $CH_2Cl_2$. The product fractions were evaporated to dryness in vacuo and the residue triturated with ether to provide the title compound: (mp 128°–132°).

TLC: $R_f$=0.49 Silica gel (10% $Et_2O$ in $CH_2Cl_2$).
NMR: Consistent with structure.
HPLC: >99.0% pure.
MS: Molecular ion observed @ m/e=377.
Anal. Calc'd for $C_{25}H_{31}NO_2$: C, 79.54; H, 8.28; N, 3.71. Found: C, 79.58; H, 8.37; N, 3.69.

EXAMPLE 23

1'-((4-Fluorophenyl)sulfonyl)spiro(1H-indene-1,4'-piperidine)

Spiro(1H-indene-1,4'-piperidine) (40 mg, 0.18 mmol) was suspended in $CH_2Cl_2$ (2 ml) and treated with triethylamine (52.6 µl, 0.378 mmol) followed by 4-fluorobenzenesulfonyl chloride (38.6 mg, 0.198 mmol). The reaction was stirred 1 hr at ambient temperature and chromatographed on a silica gel column eluted with 20% hexane in $CH_2Cl_2$. The product fractions were evaporated to dryness in vacuo and the residue crystallized from ether to provide the title compound: (mp 169°–174°).

TLC: $R_f$=0.31 Silica gel (20% hexane in $CH_2Cl_2$).
NMR: Consistent with structure.
HPLC: >97.2% pure.
MS: Molecular ion observed @ m/e=343.
Anal. Calc'd for $C_{19}H_{18}FNO_2S$: C, 66.45; H, 5.28; N, 4.08. Found: C, 66.56; H, 5.36; N, 4.09.

EXAMPLE 24

1'-((4-Chlorophenyl)sulfonyl)spiro(1H-indene-1,4'-piperidine)

The procedure of example 23 was carried out using 4-chlorophenylsulfonyl chloride (41.8 mg, 0.198 mmol) in place of 4-fluorobenzenesulfonyl chloride. Chromatographic elution was with 25% hexane in $CH_2Cl_2$. The title compound was crystallized from ether: (mp 179°–181°).

TLC: $R_f$=0.31 Silica gel (30% hexane in $CH_2Cl_2$).
NMR: Consistent with structure.
HPLC: >98.6% pure.
MS: Molecular ion observed @ m/e=359.
Anal. Calc'd for $C_{19}H_{18}ClO_3S$: C, 63.41; H, 5.04; N, 3.89. Found: C, 63.37; H, 4.91; N, 3.90.

EXAMPLE 25

1'-(3 S, 4 S-4-t-Boc-amino-3-hydroxy-6-methylheptanoyl)-spiro-(1H-indene-1,4'-piperidine)

The procedure of example 22 was carried out using 3 S, 4 S-Boc-statine (82.0 mg, 0.298 mmol) in place of (+)-camphoracetic acid. The chromatographed product (11% $Et_2O$ in $CH_2Cl_2$) was evaporated to dryness in vacuo and the residue lyophilized with dioxane to provide the title compound as a solid: (mp 50°–75°).

TLC: $R_f$=0.34 Silica gel (15% $Et_2O$ in $CH_2Cl_2$).
NMR: Consistent with structure.
HPLC: >96.7% pure.
Anal. Calc'd for $C_{26}H_{38}N_2O_4$: C, 70.55; H, 8.65; N, 6.33. Found: C, 70.37; H, 8.78; N, 6.22.

EXAMPLE 26

1'-(((2-Hydroxy-1,7,7-trimethylbicicylo(2.2.1)-hept-3-yl)methyl)carbonyl)spiro(1H-indene-1,4'-piperidine)

1'-(((2-Oxo-1,7,7-trimethylbicicylo(2.2.1)-hept-3-yl)-methyl)carbonyl)spiro(1H-indene-1,4'-piperidine) (Example 22) (47.5 mg, 0.126 mmol) was dissolved in THF (3 ml) and treated with lithium aluminum hydride (126 μl of a 1.0M solution in THF; 0.126 mmol). The solution was stirred 5 min at ambient temperature, quenched with water, acidified with 1M HCl, and extracted with ether. The ether layer was washed with brine, dried over sodium sulfate, filtered, and evaporated to dryness in vacuo. The residue was chromatographed on a silica gel column eluted with 10% $Et_2O$ in $CH_2Cl_2$. The product fractions were evaporated to dryness and the residue crystallized from hexane: (mp 137°–139°).

TLC: $R_f$=0.43 Silica gel (10% $Et_2O$ in $CH_2Cl_2$).
NMR: Consistent with structure.
HPLC: >99.6% pure.
MS: Molecular ion observed @ m/e=379
Anal. Calc'd for $C_{25}H_{33}NO_2$: C, 79.11; H, 8.76; N, 3.69. Found: C, 78.80; H, 8.86; N, 3.64.

EXAMPLE 27

(1S)-1'-(((7,7-Dimethyl-2-oximinobicicylo(2.2.1)-hept-1-yl)methyl)sulfonyl)spiro(1H-indene-1,4'-piperidine)

(1S)-1'-(((7,7-Dimethyl-2-oxobicicylo(2.2.1)-heptl-yl)methyl)sulfonyl)spiro(1H-indene-1,4'-piper-idine) (0.4 g, 1 mmol), hydroxylamine hydrochloride (0.4 g, 5 mmol), and potassium hydroxide (2 g, 35.7 mmol) were combined in 95% ethanol (20 ml) and stirred at 70° for 3 hr. The suspension was cooled to ambient temperature, diluted with water (75 ml), stirred for 20 min, and filtered. The solid was dried in vacuo at ambient temperature overnight: (mp 181°–185°).

TLC: $R_f$=0.40 Silica gel (40% EtOAc in hexane).
NMR: Consistent with structure.
HPLC: >96% pure.
MS: M+H @ m/e=415 (FAB)
Anal. Calc'd for $C_{23}H_{30}N_2O_3S \cdot 0.2H_2O$: C, 66.06; H, 7.33; N, 6.70. Found: C, 66.01; H, 7.27; N, 6.67.

EXAMPLE 28

1'-(3S,4S-4-t-Boc-amino-3-hydroxy-5-phenyl-pentanoyl)spiro(1H-indene-1,4'-piperidine)

The procedure of Example 22 was carried out using 3S,4S-Boc-AHPPA (92.2 mg, 0.298 mmol) in place of (+)-camphoracetic acid. The chromatographed compound was crystallized from ether/hexane: (mp 135°–137°).

TLC: $R_f$=0.34 Silica gel (10% $Et_2O$ in $CH_2Cl_2$).
NMR: Consistent with structure.
HPLC: >96.5% pure.
Anal. Calc'd for $C_{29}H_{36}N_2O_4$: C, 73.08; H, 7.61; N, 5.88. Found: C, 73.27; H, 7.66; N, 5.73.

EXAMPLE 29

1'-(3R,4S-4-t-Boc-amino-3-hydroxy-6-methylheptanoyl)spiro(1H-indene-1,4'-piperidine)

The procedure of Example 22 was carried out using 3R,4S-Boc-statine (82.0 mg, 0.298 mmol) in place of (+)-camphoracetic acid. The chromatographed compound was crystallized from hexane: (mp 112°–118°).

TLC: $R_f$=0.17 Silica gel (10% $Et_2O$ in $CH_2Cl_2$).
NMR: Consistent with structure.

HPLC: >98.3% pure.
Anal. Calc'd for $C_{26}H_{38}N_2O_4$: C, 70.55; H, 8.65; N, 6.33. Found: C, 70.42; H, 8.79; N, 6.08.

EXAMPLE 30

2,3-Dihydro-1'-((4-methylphenyl)sulfonyl)spiro-(1H-indene-1,4'-piperidine)

1'-((4-Methylphenyl)sulfonyl)spiro(1H-indene-1,4'-piperidine) (57.7 mg, 0.17 mmol), prepared as in example 2, was dissolved in absolute ethanol (4 ml), treated with 10% Palladium on carbon (14.2 mg), and hydrogenated at 40 psi, ambient temperature, for 3 hr. The mixture was filtered through Solka floc and the filtrate was evaporated to dryness in vacuo. The residue was crystallized from ether to provide the title compound: (m.p. 140°–142°).

MNR: Consistent with structure
HPLC: 98.3%
MS: Molecular ion @ m/e=341
Anal. Calc'd for $C_{20}H_{23}NO_2S$: C, 70.35; H, 6.79; N, 4.10. Found: C, 70.11; H, 6.77; N, 4.02.

Radioligand Binding Assays

The high affinity binding of $[^3H]OT$ ([tyrosyl, 3,5-$^3H]OT$; 30–60 Ci/mmol; New England Nuclear. Boston, MA) to uterine OT receptors was based on an assay* using a crude membrane preparation of uteri taken from diethylstilbestrol dipropionate (DES)-treated (0.3 mg/kg, ip; 18–24) rats. Competition studies were conducted at equilibrium (60 min; 22° C.) using 1 nM $[^3H]OT$ in the following assay buffer: 50 mM Tris-HCl, 5 mM $MgCl_2$, and 0.1% BSA, pH 7.4. Nonspecific binding (10% of the total binding) was determined using 1 μM unlabeled OT and the binding reaction was terminated by filtration through glass fiber filters using a cell harvester (model 7019, Skatron, Inc., Sterling, Va.).

*Fuchs, A-R; Fuchs, F; Soloff, MS. 1985 J. Clin. Endocrinol. Metab. 60:37.

The measurement of $[^3H]AVP$ ([phenylalanyl-3,4,5-$^3H]AVP$; 80–90 Ci/mmol; New England Nuclear) binding to a crude membrane preparation of male rat liver (AVP-$V_1$ sites) or kidney medulla (AVP-$V_2$ sites) was determined according to the method of Butlen et al+. Competition assays were conducted at equilibrium (30 min at 30° C.) using 1 nM $[^3H]AVP$ (liver) or 2 nM $[^3H]AVP$ (kidney) in the following assay buffer: 100 mM Tris-HCl, 5 mM $MgCl_2$, 0.1% BSA, 50 μM phenylmethylsulfonylfluoride, and 50 μg/ml bactracin, pH 8.0. Nonspecific binding (5–10% of the total binding) was determined using 10 μM unlabeled AVP, and the binding reaction was terminated by filtration as described above for the $[^3H]OT$ binding assay.

+Butlen, D; Guillon, G; Rajerison, RM; Jard, S; Sawyer, WH; Manning, M. 1978 Mol Pharmacol 14:1006.

$K_i$ values were obtained for each compound from three to six separate determinations of the $IC_{50}$ values ($K_i=IC_{50}/1+c/K_d$)# using $K_d$ values obtained from saturation binding assay: $[^3H]OT$ (uterus), 0.7 nM; $[^3H]AVP$ (liver), 0.4 nM; $[^3H]AVP$ (kidney), 1.4 nM.

Cheng, Y-C; Prusoff, WH; 1973 Biochem Pharmacol 22:3099.

TABLE I

| Compound of | Inhibition (μM)* | | |
|---|---|---|---|
| | | Vasopressin | |
| Example # | Oxytocin | V1 | V2 |
| 2 | $IC_{50}$ = 4.7 | $IC_{50}$ = 39 | $IC_{50}$~100 |
| 3 | $IC_{50}$ = 1.2 | 27% @ 10 | 14% @ 10 |
| 4 | $IC_{50}$ = 5.96 | 0% @ 10 | 11% @ 10 |

TABLE I-continued

| Compound of Example # | Inhibition (μM)* Oxytocin | Vasopressin V1 | V2 |
|---|---|---|---|
| 5 | $IC_{50} > 3.0$ | — | — |
| 6 | $IC_{50} = 1.5$ | 2% @ 10 | 3% @ 10 |
| 7 | $IC_{50} = 2.4$ | 0% @ 10 | 6% @ 10 |
| 8 | $IC_{50} = 10.0$ | — | — |
| 9A | $IC_{50} = 0.53$ | 48% @ 10 | 18% @ 10 |
| 9B | $IC_{50} = 1.17$ | 30% @ 10 | 2% @ 10 |
| 10A | $IC_{50} = 3.86$ | 2% @ 10 | 10% @ 10 |
| 10B | $IC_{50} = 2.47$ | 9% @ 10 | 11% @ 10 |
| 11 | $IC_{50} = 0.49$ | 54% @ 10 | 23% @ 10 |
| 12 | 53% @ 10 | — | — |
| 13 | $IC_{50} = 0.46$ | 45% @ 10 | 5% @ 10 |
| 14 | $IC_{50} = 2.76$ | 37% @ 10 | 12% @ 10 |
| 15 | $IC_{50} = 0.47$ | $IC_{50} \sim 9$ | 17% @ 10 |
| 16 | $IC_{50} = 4.0$ | 51% @ 10 | 18% @ 10 |
| 17 | 65% @ 10 | — | — |
| 19 | $IC_{50} = 0.35$ | 54% @ 10 | 20% @ 10 |
| 20 | $IC_{50} = 0.57$ | $IC_{50} = 89$ | $IC_{50} = 83$ |
| 21 | $IC_{50} = 0.39$ | — | — |
| 22 | 35% @ 1 | 3% @ 10 | 3% @ 10 |
| 23 | 65% @ 10 | 0% @ 10 | 6% @ 10 |
| 24 | 35% @ 1 | 30% @ 10 | 19% @ 10 |
| 25 | 50% @ 10 | 33% @ 10 | 7% @ 10 |
| 26 | 19% @ 1 | 11% @ 10 | 10% @ 1 |
| 27 | $IC_{50} = 0.49$ | 52% @ 10 | 21% @ 10 |
| 28 | 21% @ 1 | 18% @ 10 | 21% @ 10 |
| 29 | 51% @ 10 | 78% @ 10 | 13% @ 10 |
| 30 | 68% @ 10 | 67% @ 100 | 47% @ 100 |

*Inhibition is expressed either as $IC_{50}$ in μM, or as % inhibition @ a specified concentration of the test compound (μM). The $IC_{50}$ is the concentration of the text compound which inhibits specific binding by 50%. The % inhibition at a specified concentration of the test compound is that percentage of specific binding which is inhibited by said concentration of said test compound.

What is claimed is:

1. A compound having the formula:

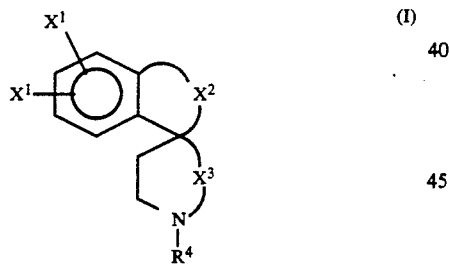

(I)

wherein:

$X^1$ is hydrogen, $C_{1-6}$ linear or branched chain alkyl, lower alkenyl, lower alkynyl, $-X^4COOR^5$, $-X^5$-cycloloweralkyl, $-X^4NR^6R^7$, $-X^4CONR^6R^7$, $-X^4CN$, $-X^4CF_3$, hydroxy, cyano, amino, nitro, loweracylamino, halogen or lower alkoxy;

$X^2$ is

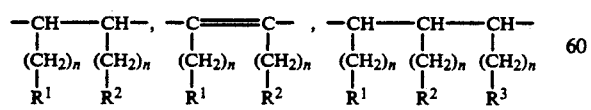

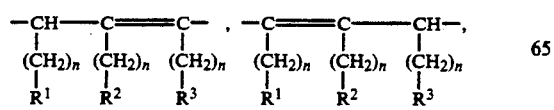

-continued $-\overset{O}{\underset{\underset{R^1}{(CH_2)_n}}{\overset{\|}{C}}}-O-$, $-\overset{O}{\overset{\|}{C}}-O-$, $-N-\overset{O}{\overset{\|}{C}}-$;
   $\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;\;R^5$ $X^3$ is $-CH_2-$, $-CH_2-CH_2-$, $-\overset{R^1}{\underset{}{CH}}-$, $-\overset{R^1}{\underset{}{CH}}-CH_2-$;

$R^1$, $R^2$ and $R^3$ are independently hydrogen, a $C_{1-6}$ linear or branch chained alkyl, 2-pyridyl, 3-pyridyl, 4-pyridyl, or a substituted or unsubstituted phenyl wherein if the phenyl is substituted there may be 1 or 2 substituents, which may be at any position on the phenyl ring and the substituents are independently halogen, $C_{1-6}$ loweralkyl, $C_{1-6}$ loweralkoxy, carboxyl, cyano, loweralkylthio, carboxyloweralkyl, nitro, $-CF_3$ or hydroxy;

$R^4$ is $-\overset{O}{\overset{\|}{C}}R^8$, $-SO_2R^8$, $-\overset{O}{\overset{\|}{C}}NHR^8$, $-SO_2NHR^8$;

$R^5$ is H, loweralkyl, cycloloweralkyl, substituted or unsubstituted phenyl, wherein if the phenyl is substituted there may be 1 or 2 substituents which may be at any position on the phenyl ring and the substituents are independently halogen, $C_{1-6}$ loweralkyl, $C_{1-6}$ loweralkoxy, nitro, or $CF_3$;

$R^6$ and $R^7$ are independently $R^5$ or in combination with the N of the $NR^6R^7$ group form an unsubstituted or mono or disubstituted, saturated or unsaturated, 4–7 membered heterocyclic ring containing a hetroatom selected from O and N or benzofused 4–7 membered heterocyclic ring containing a heteroatom selected from O and N or said heterocyclic ring and the substituent(s) is/are independently selected from $C_{1-4}$ alkyl;

$R^8$ is $-(CH_2)_n R^9$, $-(CH_2)_n$ $-\overset{X^1}{\underset{}{CH}}-(CH_2)_n-R^9$;

$R^9$ is substituted or unsubstituted phenyl wherein the substituents may be 1 or 2 of halo, loweralkyl, loweralkoxy, loweralkylthio, carboxyl, carboxyloweralkyl, nitro, $-CF_3$, hydroxy; 2-pyridyl, 3-pyridyl, 4-pyridyl; $C_{1-15}$ loweralkyl, cycloloweralkyl, $C_{5-14}$, $C_{5-14}$ bicycloloweralkyl, $C_{6-20}$ tricycloloweralkyl, any of which may contain O or N in place of one or two carbon atoms, and/or one or more double or triple bonds between adjacent carbon atoms, and any of which may be substituted or unsubstituted wherein the substituents may be independently 1 or 2 of $-OH$, $=O$, $=NOH$, $=NOCH_3$, $-NH-COCH_3$,

31
-continued

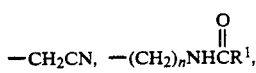

—OR¹, —NR¹₂, NHBOC, halogen, loweralkoxy, carboxy, carboalkoxy, carboxyloweralkyl, carboalkoxyloweralkyl, $(CH_2)_nNR^1_2$, substituted or unsubstituted phenyl wherein the substituents may be 1 or 2 of halo, loweralkyl, loweralkoxy, loweralkylthio, carboxyl, carboxyloweralkyl, nitro, —CF₃, hydroxy;

n is 0 to 4

X⁴ is absent or C₁₋₄ alkylene;
X⁵ is absent or C₁₋₄ alkylene; O or NH;
or the pharmaceutically acceptable salts thereof.

2. A compound of claim 1 wherein:
X¹ is hydrogen or halogen or C₁₋₆ linear or branch chained alkyl;
X² is —CH₂—CH₂—, —CH=CH—, CH₂CH₂CH₂;
X³ is —CH₂—CH₂—;
R⁴ is

R⁸ is —(CH₂)ₙR⁹;
R⁹ is substituted or unsubstituted phenyl wherein the substituents may be 1 or 2 of halo, loweralkyl, loweralkoxy, loweralkylthio, carboxyl, carboxyloweralkyl, nitro, —CF₃, hydroxy; 2-pyridyl, 3-pyridyl, 4-pyridyl; C₁₋₁₅ loweralkyl, cycloloweralkyl, polycycloloweralkyl, bicycloloweralkyl, tricycloloweralkyl, any of which may contain O or N in place of one or two carbon atoms, and/or one or more double or triple bonds between adjacent carbon atoms, and any of which may be substituted or unsubstituted wherein the substituents may be independently 1 or 2 of, —OH, =O, =NOH, —NOCH₃, —NH—COCH₃,

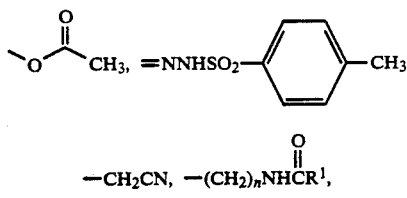

—OR¹, —NR¹₂, NHBOC, halogen, loweralkoxy, carboxy, carboalkoxy, carboxyloweralkyl, carboalkoxyloweralkyl, $(CH_2)_nNR^1_2$, substituted or unsubstituted phenyl wherein the substituents may be 1 or 2 of halo, loweralkyl, loweralkoxy, loweralkylthio, carboxyl, carboxyloweralkyl, nitro, —CF₃, hydroxy;

n is 0 to 2.

3. A compound selected from the group consisting of:
1'-((4-methylphenyl)sulfonyl)spiro-(1H-indene-1,4'-piperidine);
1'-((4-bromophenyl)sulfonyl)spiro-(1H-indene-1,4'-piperidine);
1'-((4-methoxyphenyl)sulfonyl)spiro-(1H-indene-1,4'-piperidine)
2-(spiro(1H-indene-1,4'-piperidin)-1'-ylsulfonyl)-benzoic acid methyl ester

32
(1S)-1'-(((7,7-dimethyl-2-oxobicicylo-(2.2.1)hept-1-yl)-methyl)sulfonyl)spiro-(1H-indene-1,4'-piperidine)
(1R)-1'-(((7,7-dimethyl-2-oxobicicylo-(2.2.1)hept-1-yl)-methyl)sulfonyl)spiro-(1H-inddene-1,4'-piperdine)
N-tricyclo(3.3.1.1(3,7))dec-2-yl-spiro(1H-indene-1,4'-piperidine)-1'-carboxamide
(1S)-1'-(((2-hydroxy-7,7-dimethylbicyclo-(2.2.1)hept-1-yl)methyl)sulfonyl)spiro(1H-indene-1,4'-piperidine), exo isomer (Compound A) and endo isomer (Compound B)
(1R)-1'-(((2-hydroxy-7,7-dimethylbicyclo(2.2.1)hept-1-yl)methyl)sulfonyl)spiro(1H-indene-1,4'-piperidine), exo isomer (Compound A) and endo isomer (Compound B)
(1S)-1'-(((2-hydroxy-7,7-dimethyl-2-phenylbicyclo(2.2.1)hept-1-yl)methyl)sulfonyl)-spiro-(1H-indene-1,4'-piperidine)
(1S)-1'-((4,7,7-trimethyl-3-oxo-2-oxabicyclo-(2.2.1)hept-1-yl)carbonyl)spiro(1H-indene-1,4'-piperidine)
exo-(1S)-1'-(((2-hydroxy-2,7,7-trimethylbicyclo-(2.2.1)hept-1-yl)methyl)sulfonyl)-spiro(1H-indene-1,4'-piperidine)
N-(2-(2,3-dihydro-1H-inden-1-yl)ethyl)-7,7-dimethyl-2-oxo-bicyclo(2.2.1)heptane-1-methanesulfonamide
(1S)-1'-(((2-ethyl-2-hydroxy-7,7-dimethylbicyclo(2.2.1)hept-1-yl)methyl)sulfonyl)-spiro-(1H-indene-1,4'-piperidine)
exo-N-(2-(2,3-dihydro-1H-inden-1-yl)ethyl)-2-hydroxy-7,7-dimethylbicyclo(2.2.1)heptane-1-methanesulfonamide
exo-N-(2-(1H-inden-1-yl)ethyl)-2-hydroxy-7,7-dimethylbicyclo(2.2.1)heptane-1-methanesulfonamide
(1S(1.alpha.,2.alpha.,4.alpha.))-2-hydroxy-7,7-dimethyl-1-((spiro(1H-indene-1,4'-piperidin)-1'-ylsulfonyl)methyl)bicyclo-(2.2.1)heptane-2-acetic acid ethyl ester
(1S(1.alpha.,2.alpha.,4.alpha.))-2-hydroxy-7,7-dimethyl-1-((spiro(1H-indene-1,4'-piperidin)-1'-ylsulfonyl)methyl)bicyclo-(2.2.1)heptane-2-acetic acid methyl ester
(1S(1.alpha.,2.alpha.,4.alpha.))-2-hydroxy-7,7-dimethyl-1-((spiro(1H-indene-1,4'-piperidine)-1'-ylsulfonyl)methyl)-bicyclo-(2.2.1)heptane-2-acetic acid
exo-(1S-(1.alpha.,2.alpha.,4.alpha.))-2,3-dihydro-1'-(((2-hydroxy-7,7-dimethylbicyclo(2.2.1)hept-1-yl)-methyl)sulfonyl)spiro(1H-indene-1,4'-piperidine)
1'-(((2-oxo-1,7,7-trimethylbicicylo(2.2.1)-hept-3-yl)-methyl)carbonyl)spiro(1H-indene-1,4'-piperidine)
1'-((4-fluorophenyl)sulfonyl)spiro-(1H-indene-1,4'-piperidine)
1'-((4-chlorophenyl)sulfonyl)spiro(1H-indene-1,4'-piperidine)
1'-(3S,4S-4-t-Boc-amino-3-hydroxy-6-methylheptanoyl)-spiro-(1H-indene-1,4'-piperidine)
1'-(((2-hydroxy-1,7,7-trimethylbicicylo-(2.2.1)-hept-3-yl)methyl)carbonyl)spiro(1H-indene-1,4'-piperidine)
(1S)-1'-(((7,7-dimethyl-2-oximinobicicylo-(2.2.1)-hept-1-yl)methyl)sulfonyl)spiro(1H-indene-1,4'-piperidine)
1'-(3S,4S-4-t-Boc-amino-3-hydroxy-5-phenyl-pentanoyl)spiro(1H-indene-1,4'-piperidine)
1'-(3R,4S-4-t-Boc-amino-3-hydroxy-6-methyl-heptanoyl)spiro(1H-indene-1,4'-piperidine)
2,3-dihydro-1'-((4-methylphenyl)sulfonyl)-spiro-(1H-indene-1,4'-piperidine).

4. A pharmaceutical composition which comprises a therapeutically effective amount of a compound of claim 1 effective to treat preterm labor and dysmenorrhea or to stop labor preparatory to caesarian delivery and a pharmaceutically acceptable carrier.

* * * * *